US007048792B2

(12) United States Patent
Axen et al.

(10) Patent No.: US 7,048,792 B2
(45) **Date of Patent: *May 23, 2006**

(54) METHOD OF MAKING STRUCTURED CERAMIC COATINGS AND COATED DEVICES PREPARED WITH THE METHOD

(75) Inventors: Niklas Axen, Jarlasa (SE); Kajsa Bjorklund, Uppsala (SE); Leif Hermansson, Uppsala (SE); Hakan Engqvist, Knivsta (SE)

(73) Assignee: Cerbio Tech AB, Uppsala (SE)

(*) Notice: Subject to any disclaimer, the term of this patent is extended or adjusted under 35 U.S.C. 154(b) by 125 days.

This patent is subject to a terminal disclaimer.

(21) Appl. No.: 10/691,542

(22) Filed: Oct. 24, 2003

(65) Prior Publication Data

US 2004/0146752 A1 Jul. 29, 2004

(30) Foreign Application Priority Data

Oct. 31, 2002 (SE) .................................... 0203223

(51) Int. Cl.
*C04B 11/28* (2006.01)
*A61F 2/02* (2006.01)

(52) U.S. Cl. ...................... 106/692; 428/701; 428/702; 428/704; 428/697; 428/323; 623/11.11; 623/23.56; 623/23.62

(58) Field of Classification Search ................ 428/701, 428/697, 702, 704, 323; 106/692; 623/11.11, 623/23.56, 23.62
See application file for complete search history.

(56) References Cited

U.S. PATENT DOCUMENTS 5,480,438 A 1/1996 Arima et al.

FOREIGN PATENT DOCUMENTS

| | | |
|---|---|---|
| SE | 0104440-3 | 12/2001 |
| SE | 0104441-1 | 12/2001 |
| SE | 02006377 | 3/2002 |
| SE | 0201921-4 | 12/2003 |
| WO | WO 00/21489 | 4/2000 |
| WO | 04/000239 | 12/2003 |

*Primary Examiner*—Ling Xu
(74) *Attorney, Agent, or Firm*—Young & Thompson

(57) ABSTRACT

The invention describes a low temperature method for producing multi-layered or multi-phased coatings. With the technique according to the present invention, surface coatings with controlled variations in terms of chemical composition, phase composition, porosity, surface roughness, mechanical properties, biocompatibility, etc can be achieved. The method of coating a substrate surface comprising the steps of preparing one powder mixture, or several powder mixtures having different chemical composition, wherein at least one of said powder mixtures comprise a non-hydrated hydraulic ceramic powder binder phase, pretreating a substrate surface, to increase the adhesion between the substrate and the ceramic coating, applying one or more different layers on top of each other of the non-hydrated powder mixture on the substrate, and finally, hydrating the powder layer/layers in a curing agent containing ions of carbonates, phosphates or fluorides.

7 Claims, 1 Drawing Sheet

METHOD OF MAKING STRUCTURED CERAMIC COATINGS AND COATED DEVICES PREPARED WITH THE METHOD

THE FIELD OF THE INVENTION

The present invention relates to a method for low temperature deposition of multi-phase and multi-layered coatings of ceramic compositions with hydraulic binder phases on substrates, which may be metals, polymers as well as ceramics.

BACKGROUND OF THE INVENTION

Some bioceramics are of particular interest within orthopaedics and odontology, e.g. hydroxyapatite, fluoroapatite, calcium phosphates, calcium carbonate and Bioglass®. These materials can also be made more or less bio-resorbable, i.e. they may be dissolved in the body and replaced by natural tissues. This group of ceramics is explored e.g. for orthopaedic metal implants coated with a surface layer of hydroxyapatite, and various bone graft materials based on calcium phosphates and/or calcium carbonates e.g.

Precipitation of apatite in ceramic materials has also been described. A material system based on calcium aluminate and a hydration liquid containing water solvable phosphates to enhance apatite formation are described in: "System for dental filling materials or implant material, and powder material and hydration liquid" (SE 0201920-6), and "Bonding system for dental filling material or implant material, and powder material and hydration liquid and method to create bonding" (SE 0201921-4). These patent applications do not include material compositions for coatings or techniques to achieve coatings.

A range of established surface coating techniques have been described. The most established techniques for deposition of ceramic coatings are Chemical Vapour Deposition, Physical Vapour Deposition, Thermal Spraying, Plasma Spraying and Electrolytic Deposition. Surface coatings may also be produced with powder technology.

A great disadvantage with these techniques for deposition of ceramic coatings, with the exception of electrolytic deposition, is the elevated temperatures involved in their processing. This sets limitations to the selection of substrate materials, and to the chemical structures and phases that can be achieved. To the disadvantage also counts the complexity of the required equipments, such as the gas-tight vacuum arrangements needed for chemical and physical vapour deposition, and the high-temperature and presses required in powder technology.

A recently developed method for the deposition of coatings based on chemically bonded ceramics is described in the patent applications SE-0104440-3, "Coating method and coated devices" (filed December 2001); and SE-0200637-7, "Ceramic surface layers and coated devices (filed March 2002). These patent applications describe a coating deposition method comprising the steps: pre-treatment of substrate; preparation of curable slurry with hydraulic components, deposition of the slurry as a coating on a substrate and hardening of the coating through hydration. Alternatively, layers of non-hydrated hydraulic powders are deposited on the substrate, and hydrated in an additional step.

U.S. Pat. No. 5,480,438-A, filed Sep. 22, 1993, describes ceramic multi-layers comprising a metallic implant base coated with two bioactive layers. The inner layer can be comprised of calcium aluminate and the outer layer of apatite and/or calcium phosphate. This multi-layer is manufactured by other methods, mainly plasma spraying, than the methods used in the present application. Nor does U.S. Pat. No. 5,480,438-A disclose multi-layers comprised of hydrated ceramic.

SUMMARY OF THE INVENTION

The present invention relates to a method of making structured ceramic coatings and coated devices prepared with the method. More specifically, the present invention relates to a low temperature method for producing multi-layer or multi-phase (multi-structured) coatings and devices covered with such coatings, such as those depicted in FIG. 1. With the technique according to the present invention, surface coatings with controlled variations in terms of chemical composition, phase composition, porosity, surface roughness, mechanical properties, biocompatibility, etc can be achieved.

The present invention provides a method for producing a multi-structured and/or multi-phased ceramic coating in one step. In a basic form, said method comprises application of a non-hydrated ceramic component (or a mixture comprising at least one hydraulic component, which is preferably a phase of calcium aluminate) on a substrate and curing said aggregate using a water-based solution comprising ions from other compounds. By this method, a multi-structured, a multi-phased ceramic coating, or a combination of the both, can be obtained.

The method according to the present invention can be combined with any coating method involving application of one or more non-hydrated ceramic materials on a substrate. The method according to the present invention is also applicable if the applied ceramic layers are composed of different ceramic materials or comprise mixtures.

The surface coating method according to the present invention is preferably used for producing a biocompatible coating. This biocompatible coating may suitably be used for producing general implants, or specifically implants for orthopaedic and dental applications. The present invention also relates to a device, the surface of which has been coated with a biocompatible coating according to the present invention. The biocompatible coatings may also be used as carriers of therapeutically active drugs, as well as for applications within the fields of micro-structure technology and tribology.

DETAILED DESCRIPTION OF THE INVENTION

Figure 1:
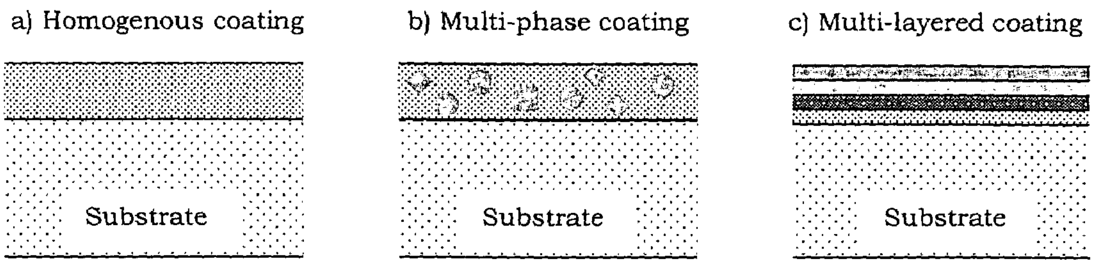
FIG. 1. Schematic general drawings of a) homogenous coating, b) multi-phase coating, and c) multi-layered coating, which can be achieved using the coating method according to the present invention.
Figure 2:
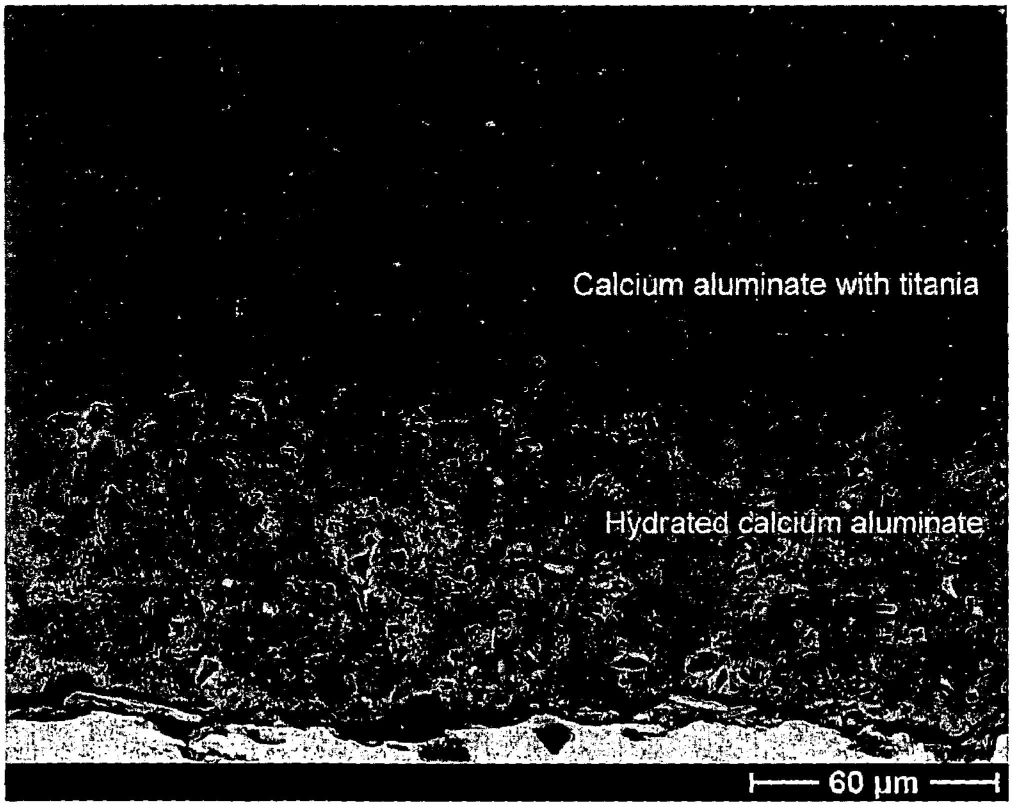
FIG. 2. Scanning electron cross-section image of double layered coating consisting of a pure hydrated calcium aluminate layer in contact with the substrate and an outer layer of calcium aluminate with 10 wt. % titania.

The present invention relates to a low temperature method to produce surface coatings based on chemically bonded hydraulic ceramics, in particular all phases of calcium aluminate are applicable to the invention. The method may be used to create coatings consisting of several phases or consecutive layers by in situ formation of biocompatible and bioactive phases. The present invention describes different ways of controlling the microstructure, porosity, thickness, surface roughness, phase composition and biocompatibility of a coating system.

Specific for the present invention is the control of the in situ formation of multi-structured biocompatible compounds during the production of the coatings by controlling the chemical environment affecting the hydration. The chemical environment during hydration may be controlled both with additives in the powder and in the hydration liquid.

The method according to the present invention allows the deposition of coating structures combining mechanically strong and chemically stable compounds (primarily hydrated calcium aluminate) with osseocompatible or bioresorbable compounds, such as hydroxyapatite and calcium carbonate. Coatings may be designed e.g. with an outer layer of the bioresorbable substance, and an inner layer of a hydrated ceramic having better mechanical properties and adhesion to the substrate.

One object of the present invention is to provide a surface coating method comprising the steps of preparing one powder mixture, or several powder mixtures having different chemical composition (in terms of stochiometry, phases and grain sizes), wherein at least one of said powder mixtures comprise a non-hydrated hydraulic ceramic powder binder phase, pre-treating a substrate surface, to increase the adhesion between the substrate and the ceramic coating, applying one single layer or several layers on top of each other of the non-hydrated powder mixture on the substrate, and hydrating the powder layer/layers in a curing agent containing ions of carbonates, phosphates or fluorides. Said non-hydrated hydraulic ceramic powder essentially comprises calcium aluminate, calcium silicate or calcium sulphate or mixtures thereof.

The present invention provides an improved coating method for coating various devices, such as medical devices, which improved coating method is related to the methods described in the earlier patent applications SE-0104440-3, "Coating method and coated devices" (filed December 2001); and SE-0200637-7, "Ceramic surface layers and coated devices (filed March 2002).

Due to the simple application technique for the powders and the low temperatures required for hydration, the chemical composition and the phases of compounds contained in such a composition, as well as the microstructure and porosity of the different layers, can be controlled much better than with the prior art techniques.

Throughout this application the term "biocompatibility" is used a number of times implying certain properties on the material or surface in question. However, it should be noted that biocompatibility is used as a generic term for the different properties that are required or desirable for materials that are to be in contact with biological tissues. Moreover, the materials have also to be used/prepared in the right way and for suitable applications. Another frequently used term is "osseo-compatible", which implies that a material is especially advantageous for use in contact with bone tissue. The term "bioactive" means that a material being bioactive stimulates the in-growth of an implant in for example bone tissue. The term Bioglass® which is used several time in the description is a trade name for a family of phosphorous glasses of good biocompatibility.

Multi-phase and Multi-layered Coatings

In addition to homogenous single-phase coatings, improved performance is often achieved with multi-phase and multi-layered coatings systems. Reasons to use such coating systems may be to improve the adhesion to the substrate, to increase the toughness, hardness or biocompatibility; to reduce internal stresses in the coatings; or to control volumetric changes during coating manufacturing. The concepts of multi-phase and multi-layered coatings are illustrated by FIG. 1.

The different phases or individual layers may be composed of one or several of the following compounds: calcium aluminates, calcium aluminate hydrates, other hydraulic phases, e.g. calcium sulphate and calcium silicate, fluorapatite, hydroxyapatite, other apatites, calcium phosphates, calcium carbonates, carbonates-apatites mixed phases, Bioglass®, inert phases (non-hydrating phases and calcium aluminate).

The most preferred hydraulic cement used with the method according to the present invention is various forms of calcium aluminate. But the method is applicable also on other hydraulic cements, such as silicates and sulphates.

Like in methods disclosed in previous patent applications SE-0104440-3, "Coating method and coated devices" (filed December 2001); and SE-0200637-7, "Ceramic surface layers and coated devices (filed March 2002), the method comprises the following steps:

Pre-treatment of substrate.

Preparation of powder particles and dispersions of these in a liquid.

Deposition of powders particles on a substrate surface, in single or multiple layers Hydration of hydraulic component with water, water based solutions or evaporated water.

However, in the method according to the present invention the step of depositing powders particles the substrate surface differs from the above-mentioned methods in that layers of different chemical composition are applied on top of each other. Furthermore, the step of hydrating the hydraulic component has been modified in that the hydration medium has additions of different compounds generating specific ions when dissolved in e.g. water, or additions of similar substances to the powder material.

Pre-treatment of the Substrate

The substrate pre-treatment follows the same procedures as described in SE-0104440-3, "Coating method and coated devices" (filed December 2001).

The pre-treatment step is preferably performed with wet or dry sand blasting generating a surface roughness with $R_a$-values, in the range of 0.1 to 10.0 μm. Also other techniques resulting in similar random surface structures may be applicable, e.g. etching processes, electrolytic processes or abrasive surface treatments. The aim of the blasting is to achieve the anchoring of the coating on the substrate. Also blasting with particles of hydraulic ceramics, preferably CA, is an alternative; this provides seed points (embedded ceramic powder or particles) for the following hydration of the applied ceramic powder. Optionally, but not necessary, the substrate surface may also be pre-treated with hydration accelerating compounds, such as LiCl or other accelerators known within the field. The purpose of the pretreatment with such an accelerator is to initiate the hydrating process in a controlled way directly on the substrate surface, whereby porosity, cracking etc. is avoided at the coating/substrate interface.

The substrate used is according to the present invention Ti or alloys thereof, stainless steel, Co—Cr alloys, another biocompatible metal, polymeric or ceramic material, or any combination thereof.

Preparation of Powder Mixtures and Dispersions of These

Preparation of the powder particles involves creation of a selected composition, phase structure and grain size of the hydraulic cement, which is preferably calcium aluminate or calcium silicates. In a basic form of the present invention, the ceramic powder comprises only hydraulic grains of calcium aluminate, of which several stoichiometries exist. Powders consisting of $C_3A$, $C_{12}A_7$, CA, $CA_2$ and $CA_6$, where C stands for CaO and A for $Al_2O_3$, are all applicable to the present invention. Such powders are commercially available products.

To control the formation of apatites and carbonates during the coating production, all powder additives providing phosphate, fluoride or carbonate ions are of relevance to the invention, these may be calcium phosphates, hydroxyapatite, fluoroapatite, calcium carbonates or other carbonates, carbonates-apatites, Bioglass®, sodium phosphates.

Said surface coating method may optionally comprise the step of preparing a powder mixture comprising adding particles or powder of one or more biocompatible or bioactive materials composed of particles or powder of one or several phases containing phosphates, flouorides or carbonates, calcium carbonate, calcium phosphate, apatite, fluoroapatite, carbonates-apatites, hydroxyapatite and Bioglass®.

In addition to the hydraulic component and the additives controlling the formation of apatites and carbonates, the powder mixture may also contain additives controlling mechanical properties, expansion, curing time, etc.

A non-hydraulic, i.e. non-hydrating, filler may be added as described in our co-pending Swedish patent application SE-0 104 441-1 with the title "Ceramic material and process for manufacturing". The non-hydraulic filler may comprise calcium titanate or any other ternary oxide of perovskite structure according to the formula $ABO_3$, where O is oxygen and A and B are metals, or any mixture of such ternary oxides. A in the perovskite structure is selected from the group comprising Mg, Ca, Sr or Ba, and that the B in the perovskite structure is selected from the group comprising Ti, Zr, or Hf. The non-hydraulic filler should be present in an amount of less than 30 vol. %, preferably less than 10 vol. % of the total volume of the ceramic ingredients. But, all material compositions disclosed in said application also apply as coating materials in the present invention.

Also, the expansion controlling additives described in the patent application PCT/SE99/01803, "Dimension stable binding agent systems", are relevant to the present invention, primarily calcium silicates and fumed silica (very finely grained silica).

The surface coating method according to the present invention may also optionally include removing residual water and/or organic material in the powder material.

According to the present invention the surface roughness and porosity are controlled by the choice of particle size of the powder/particle mix. Thus, the method according to the present invention optionally comprises reducing the powder grain size. Small grain sizes allow for smoother coatings and for even coverage of micro-structured surfaces. When these properties are required, the powder grain size is preferably below 10 μm and more preferably between 0.1 and 3 μm. Larger grains and agglomerated grains also produce more porous coatings.

The applied non-hydrated ceramic layer/layers may also be compacted prior to the final hydration. Such compacting can be achieved by using cold isostatic pressing (CIP), hot isostatic pressing (HIP), or by passing a laser beam across the surface. After the compaction step, the degree of compaction of the powder layer is increased between 30 and 80% and the porosity reduced to 30–45 vol %.

According to the present invention the surface roughness is also controlled by the choice of dispersion liquid for the particle mix. Dispersion liquids of relevance are water, carbonated water, alcohols, oils, acetone, other hydrocarbons, buffer solutions, phosphate solutions, plasticizers, etc. Properties of the liquid to consider are viscosity, vapour pressure, dispersion effects as well as wettability to powder particles and to substrate. Water or water-based solvents lead to an immediate start of the hydration. Non-water solvents are combined with post-curing, meaning that the actual curing is performed in a separate step.

Ethanol produces smoother surfaces than acetone due to better dispersion ability. For water-based liquids, the surfaces structure is controlled by the use of water dissolvable dispersing agents and plasticisers.

In the case of curing in water or water-based solutions, the chemistry and phase compositions of the cured coating are controlled through the concentrations of carbon dioxide or carbonate, phosphate or fluoride salts. The higher the concentration of carbonate ions, the more calcium carbonates may potentially be formed. The higher the concentration of phosphates or fluorides, the more hydroxyapatite or fluorapatite is formed during hydration.

For the creation of multi-layered coatings, powder mixtures of different chemical composition and solvents may be prepared for deposition in several subsequent steps.

When it is desired to achieve a multi-structure coating using only one powder layer, the phase composition of the coating can according to the present invention be controlled by adding specific ions to the curing agent. These ions can be provided by adding carbon dioxide or carbonate, phosphate or fluoride salts to the curing agent. The curing agent may be performed a liquid or a gas, and is preferably a water-based agent, such as a water solution or vapour. Optionally, a component which accelerates or retards the hardening process may be added to the curing agent or the powder material.

Deposition of Powders Particles on Substrate Surface

The powder-solvent mixture is applied to the substrate as one or several thin layers. Various deposition techniques may be used, e.g. dipping, spraying, etc. All deposition techniques described in our co-pending Swedish patent application SE-0200637-7, "Ceramic surface layers and coated devices (filed March 2002) are of relevance to the present invention.

The application of the powder material on the substrate surface is performed by a thermal spray technique, PVD or CVD deposition techniques, or applied as a tape prepared by tape casting.

The thickness of the coating is controlled either by the particle size, the dispersion of the particles and the powder-to-solvent ratio. For thick coatings multiple dipping or spraying can be performed.

After deposition of the particle mix, the solvent is evaporated. The evaporation may be performed by letting the particle mixture stand at room temperature in normal atmosphere, but the evaporation process is accelerated at higher temperatures.

The deposited surface coating according to the present invention has a thickness in the order of 0.1–500 μm, and preferably less than 50 μm.

Post-hydration

The most relevant procedure of the present invention to cure the deposited particle layer or layers is by post-hydration in a separate step in a water solution, water vapour or an atmosphere of controlled humidity.

Also the temperature affects the curing procedure. Most relevant for the invention are temperatures between 0° C. and 100° C. Preferably, the curing is performed in the range of 20° C. to 70° C.

During post-hydration the amounts of calcium carbonate and calcium aluminocarbonates are controlled by the presence of carbon dioxide. By controlling the hydrogen-carbonate concentration in the hydration water or in the vapour, the amount of the calcium carbonate within the coating and at the coating surface is controlled. By hydrating the coatings in carbonated water the top-surface layer will mainly consist of calcium carbonate. If the hydration takes place with decarbonated water the calcium carbonate formation is suppressed, resulting in a low calcium carbonate content in the surface layer.

Hydration can also be performed in phosphate ion rich solutions, such as phosphate buffer solutions or simulated body fluids, to produce calcium phosphates and apatites. Fluoride solutions produce calcium fluoride.

However, during hydration, many other phases may form as a result of the details of the chemical environment. For example, the presence of carbon oxide, either as atmospheric $CO_2$ and/or as carbonic acid in the hydration water or as a carbonate compound, may lead to the formation of calcium carbonates or calcium carboaluminates during the hydration, in addition to the calcium aluminate hydrates. The formation of carbonates interact with the hydration of the aluminate, e.g. following the reactions:

$$CAH_{10}+CO_2 \rightarrow CaCO_3+AH_3+7H_2O$$

$$C_3AH_6+3CO_2 \rightarrow 3CaCO_3+AH_3+3H_2O$$

Consequently, the presence of carbonic acid in the hydration water or atmospheric $CO_2$, controls the amount of carbonates or carboaluminates formed during and after hydration. The formation of calcium carbonate and calcium carboaluminates can be suppressed or enhanced by controlling the access to carbonic compounds in the hydration environment. Depending on the surrounding temperature different compounds and phases are formed. For instance, at room temperature, the calcium aluminate hydrates are more stable than the calcium carbonates. In the presence of carbon, the hydrates may still transform to carbonates over a period of time corresponding to several months. At 37° C. the calcium aluminate hydrates are still more stable, but the carbonate formation proceeds faster than at room temperature, over a period of time of some days or weeks. At 60 C° or higher the carbonation reactions progress much further and faster, and more calcium carbonate than calcium aluminate hydrates may be formed. Hence the detailed phase composition can be steered with the curing temperature. The entire temperature range from 0 to 100 C° is applicable according to the purposes of the present invention.

Formation of calcium carbonate during hydration of calcium aluminate is of particular interest due to at least two reasons. First, calcium carbonate is a resorbable bio-ceramic; it interacts with the regeneration process of bone tissue in a living organisms. Second, controlled carbonation of the calcium aluminate hydrate has been shown to result in an increase in strength of the hydrate.

Similarly, the presence of phosphates or fluorides in the chemical environment during hydration of calcium aluminate may produce the biocompatible substances hydroxyapatite and fluoroapatite ($Ca_5(PO_4)_3OH$ and $Ca_5(PO_4)_3F$, respectively), or other calcium phosphates and flourides. The formation of these substances requires the presence of the ions: $Ca^{2+}$, $OH^-$, $H^+$ and $PO_4^{3-}$, alternatively $F^-$, during hydration, in combination with a suitable pH range (concentration of $OH^-$ and $H^+$) and temperatures. During hydration of calcium-based hydraulic systems, the $Ca^{2+}$-ions originate from the hydraulic grains and the $OH^-$ from the hydration process. The phosphate or fluoride ions may originate from the powder mixture or from the hydration liquid. $H^+$ originates from the hydration water.

This means that the calcium based hydraulic systems have the ability to in situ form calcium phosphates, hydroxyapatites, fluor apatites, calcium carbonates as a natural part of the hydration reactions, if suitable chemical environments are created. In this patent application, these known phenomena are explored as part of a method to create multi-layered coatings.

Coatings and Coated Devices

In one embodiment of the method according to the present invention a biocompatible coating is achieved comprising a binding layer in contact with the substrate comprising mainly calcium aluminate particles of less than 2 μm, a bulk layer comprising mainly calcium aluminate having a grain size between 3 and 30 μm, and an outer layer comprising a bioactive material, preferably calcium phosphate, apatite, calcium carbonate or calcium fluoride.

The biocompatible coatings may also be used as carriers of therapeutically active drugs.

The present invention also relates to a surface coated device, comprising a substrate and a surface coating covering at least a section of the substrate surface, wherein the surface coating is the biocompatible surface coating made by using the surface coating method according to the present invention and the substrate is Ti or alloys thereof, stainless steel, Co—Cr alloys, another biocompatible metal, polymeric or ceramic material, or any combination thereof. The surface coated device may be a medical device, medical device for implantation, artificial orthopedic device, spinal implant, joint implant, attachment element, bone nail, bone screw, or a bone reinforcement plate.

EXAMPLES

Example 1

The surface of a stainless steel substrate, in the form 50 mm long and 4 mm in diameter rods, were pre-treated by sand blasting with 90 mesh aluminum oxide grit to a surface roughness of $R_a$ between 0.6 and 0.7 μm.

A calcium aluminate powder from Lafarge Aluminates, Ternal White® was selected. This is a calcium aluminate with a ratio of $Al_2O_3$ and CaO of about 70/30. However, any other similar calcium aluminate powder is also possible to use for the same purpose.

The grain size of the calcium aluminate powder was reduced by ball milling. The milling reduced the size of 90% of the grains to less than 10 μm. The milling was performed with a rotating cylindrical plastic container using 10 mm in diameter silicon nitride spheres as milling medium. The milling liquid was iso-propanol. The total milling time was 72 hrs.

After milling, the milling bodies were removed by sieving and the alcohol was evaporated. Thereafter the milled powder was burnt at 400° C. for 4 hours, to remove any residual water and organic contamination.

As the bioactive component, hydroxyapatite from Merck with an average grain size of 5 μm was selected.

For the application of a graded coating, two different slurries were prepared. The first slurry, A, consisted of the milled calcium aluminate powder and ethanol mixed with in ration 1:1 by weight.

A first layer was applied by dipping the substrate in slurry A, whereafter the ethanol was evaporated in air.

The substrate was dipped once in slurry A and then air-dried. The coating was then hydrated in a closed container with carbonated water at the bottom at 60° C. for one week. Calcium aluminate phases are quickly formed, within less than an hour. The carbonated water accelerates the in situ formation of calcium carbonate on the surface. The resulting coating consists of a double-layered structure with calcium aluminate hydrates close to the substrate and calcium carbonate rich outer layer at the surface. The entire coating was approximately 50 μm in thickness, the calcium carbonate surface layer was approximately 5–10 μm. Here a double-layered structure is achieved with only one powder layer and only one hydration step and one hydration temperature.

Example 2

Stainless steel substrates and calcium aluminate powder were prepared as in Example 1.

The substrate was dipped once in slurry A and then air-dried. The sample was hydrated in a closed container with de-ionized water at the bottom at 37 ° C. for 3 days. Finally the coated sample was placed in a simulated body fluid at 37° C. for two weeks.

The simulated body fluid was a commercial version from Sigma (product D8662) buffered to pH 7.2–7.6, containing $KH_2PO_4$ (0.2 grams/Liter), NaCl (8.0 g/L), $Na_2HPO4$ (1.15 g/L), KCl (0.2 g/L), $MgCl_2.6H_2O$ (0.1 g/L) and $CaCl_2.2H_2O$ (0.133 g/L) dissolved in de-ionized water. This mixing initiates phosphatising of the coating.

After the phosphatising step the resulting coating consisted of a 20–50 μm calcium aluminate hydrate, with small amounts of non-hydrated calcium aluminate, close to the substrate, and an outer 1–2 μm thin layer of hydroxyapatite/calcium phosphate. In this example, a two-layered structure is achieved with only one powder layer and a two-step hydration procedure.

What is claimed is:

1. Biocompatible coating, comprising:

a binding layer in contact with a substrate and comprising mainly hydrated calcium aluminate particles of less than 2 μm;

a bulk layer comprising mainly hydrated calcium aluminate having a grain size between 3 and 30 μm; and an outer layer comprising a bioactive or biocompatible material.

2. Biocompatible coating according to claim 1, wherein the coating is capable of carrying drugs.

3. The biocompatible coating of claim 1, wherein said outer layer comprises one of calcium phosphate, apatite, calcium carbonate and calcium fluoride.

4. Surface coated device, comprising a substrate and a surface coating covering at least a section of the substrate surface, wherein the surface coating is a biocompatible surface coating comprising:

a binding layer in contact with the substrate and comprising mainly hydrated calcium aluminate particles of less than 2 μm;

a bulk layer comprising, mainly hydrated calcium aluminate having a grain size between 3 and 30 μm; and an outer layer comprising a bioactive or biocompatible material.

5. Surface coated device according to claim 4, wherein the substrate is Ti or alloys thereof, stainless steel, Co—Cr alloys, a biocompatible metal, polymeric or ceramic material, or any combination thereof.

6. Surface coated device according to claim 4, that is one of an artificial orthopedic device, spinal implant, joint implant, bone nail, bone screw, a bone reinforcement plate and any other implantable element.

7. The surface coated device of claim 4, wherein said outer layer comprises one of calcium phosphate, apatite, calcium carbonate and calcium fluoride.

* * * * *